United States Patent [19]

Treuner et al.

[11] 4,088,816
[45] * May 9, 1978

[54] 3-HETEROTHIO SUBSTITUTED 7-(UREIDO-HETEROACETYL) CEPHALOSPORINS

[75] Inventors: Uwe D. Treuner; Hermann Breuer, both of Regensburg, Germany

[73] Assignee: E. R. Squibb & Sons, Inc., Princeton, N.J.

[*] Notice: The portion of the term of this patent subsequent to Nov. 16, 1993, has been disclaimed.

[21] Appl. No.: 664,796

[22] Filed: Mar. 8, 1976

Related U.S. Application Data

[63] Continuation-in-part of Ser. No. 507,900, Sep. 20, 1974, abandoned.

[51] Int. Cl.² .................. C07D 501/56; A61K 31/545
[52] U.S. Cl. .......................................... 544/27; 544/4; 544/25; 424/246
[58] Field of Search ............... 260/243 C; 544/26, 27, 544/25, 4

[56] References Cited

U.S. PATENT DOCUMENTS

| | | | |
|---|---|---|---|
| 3,641,021 | 2/1972 | Ryan, Jr. | 260/243 C |
| 3,673,183 | 6/1972 | Erickson | 260/243 C |
| 3,708,479 | 1/1973 | Welch et al. | 260/243 C |
| 3,757,015 | 9/1973 | Crast, Jr. | 260/243 C |
| 3,759,904 | 9/1973 | Crast, Jr. | 260/243 C |
| 3,796,801 | 3/1974 | Guarini | 424/246 |
| 3,813,388 | 5/1974 | Crast, Jr. | 260/243 C |
| 3,819,621 | 6/1974 | Morimoto et al. | 260/243 C |
| 3,821,207 | 6/1974 | Chow et al. | 260/243 C |
| 3,833,568 | 9/1974 | Dolfini et al. | 260/243 C |
| 3,860,591 | 1/1975 | Brewer | 260/243 C |
| 3,867,380 | 2/1975 | Dunn et al. | 260/243 C |
| 3,878,204 | 4/1975 | Ochiai et al. | 260/243 C |
| 3,978,051 | 8/1976 | Dolfini | 260/243 C |
| 3,989,693 | 11/1976 | Dolfini | 260/243 C |
| 3,989,697 | 11/1976 | Dolfini | 260/243 C |
| 3,996,217 | 12/1976 | Brewer et al. | 260/243 C |
| 4,000,134 | 12/1976 | Dolfini | 260/243 C |

*Primary Examiner*—Donald G. Daus
*Assistant Examiner*—Diana G. Rivers
*Attorney, Agent, or Firm*—Lawrence S. Levinson; Merle J. Smith; Stephen B. Davis

[57] ABSTRACT

Compounds of the formula

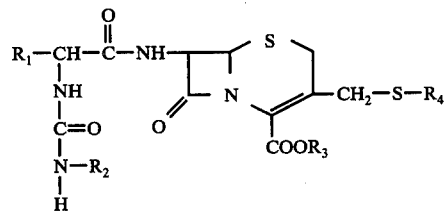

wherein $R_1$ and $R_4$ represent certain heterocyclic groups; $R_2$ is hydrogen or lower alkyl; and $R_3$ is hydrogen, lower alkyl, phenyl-lower alkyl, substituted phenyl-lower alkyl, diphenyl-lower alkyl, tri(lower alkyl)stannyl, tri(lower alkyl)silyl, a salt forming ion, or the group

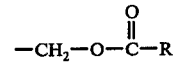

wherein R is lower alkyl, phenyl, phenyl-lower alkyl, or substituted phenyl and phenyl-lower alkyl are disclosed. These compounds are useful as antibacterial agents.

14 Claims, No Drawings

3-HETEROTHIO SUBSTITUTED 7-(UREIDO-HETEROACETYL) CEPHALOSPORINS

This application is a continuation-in-part of Ser. No. 507,900 filed on Sept. 20, 1974, now abandoned.

BACKGROUND OF THE INVENTION

Cephalosporins having a ureido acyl side chain are disclosed in U.S. Pat. Nos. 3,673,183; 3,708,479; 3,833,568; and 3,860,591. Cephalosporins substituted in the 3-position with -CH$_2$-S-hetero groups and in the 7-position with

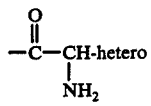

groups are disclosed as possessing antibacterial activity in U.S. Pat. Nos. 3,641,021; 3,759,904; 3,813,388; 3,821,207; 3,878,204; 3,796,801 (method of treating Enterobacter infections), etc. Also disclosed as useful intermediates are cephalosporins substituted in the 3-position with -CH$_2$-S-hetero groups and in the 7-position with a

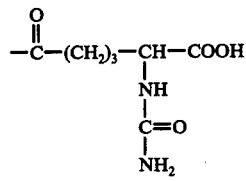

group, U.S. Pat. No. 3,819,621.

SUMMARY OF THE INVENTION

This invention relates to new cephalosporins of the formula

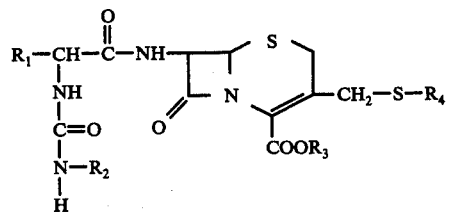

(I)

wherein R$_1$ and R$_4$ represent certain heterocyclic groups; R$_2$ represents hydrogen or lower alkyl, and R$_3$ represents hydrogen, lower alkyl, phenyl-lower alkyl, diphenyl-lower alkyl, substituted phenyl-lower alkyl, tri(lower alkyl)-stannyl, tri(lower alkyl)silyl, a salt forming ion, or the group

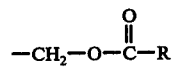

wherein R is lower alkyl, phenyl, phenyl-lower alkyl, or substituted phenyl and phenyl-lower alkyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, e.g., benzyl, phenethyl, diphenylmethyl, etc.

The substituted phenyl and substituted phenyl-lower alkyl groups include one or two (preferably only one) simple substituents selected from halogen (preferably chlorine or bromine), lower alkyl and lower alkoxy, e.g. 2-, 3- or 4-chlorophenyl, 2-, 3- or 4-bromophenyl, 3,4-dichlorophenyl, 2-methylphenyl, 4-ethoxyphenyl, 2-, 3-, or 4-chlorobenzyl, 2-, 3- or 4-ethylphenethyl, etc.

The salt forming ions represented by R$_3$ may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine.

The heterocyclics represented by R$_1$ are thienyl, furyl, pyrryl, pyridyl, thiazolyl, isothiazolyl, oxazolyl, isoxazolyl, thiadiazolyl, and tetrazolyl. They are attached at any available carbon atom as for example 2- or 3-thienyl, 2- or 3-furyl, 2- or 3-pyrryl, 2-, 3- or 4-pyridyl, 2- or 5-thiazolyl, 3- or 5-isothiazolyl, 2- or 5-oxazolyl, 3- or 5-isoxazolyl, 3- or 5-(1,2,4-thiadiazolyl), etc. Also included within the meaning of R$_1$ are such heterocyclics having a halogen (preferably Cl or Br) or a lower alkyl (preferably methyl or ethyl) substituent, i.e. 5-(1-methyltetrazolyl), 2-(5-chlorothienyl), 2-(4-chloropyrryl), etc.

The heterocyclic groups represented by R$_4$ are

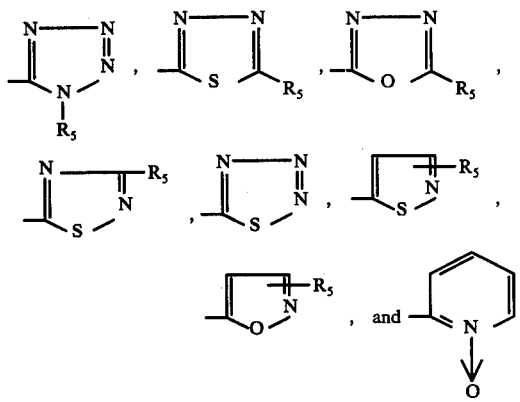

wherein R$_5$ is hydrogen or alkyl of 1 to 4 carbons.

Preferred embodiments of this invention are as follows:

R$_1$ is thienyl, furyl, pyrryl, or pyridyl.

$R_2$ is hydrogen or lower alkyl of 1 to 4 carbons.

$R_3$ is hydrogen, lower alkyl of 1 to 4 carbons, benzyl, phenethyl, diphenylmethyl, trimethylsilyl, trimethylstannyl, aluminum, alkaline earth metal, alkali metal, or

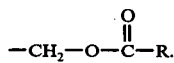

R is lower alkyl of 1 to 4 carbons, phenyl, benzyl, or phenethyl.

The most preferred embodiments are:

$R_1$ is thienyl or pyridyl, especially 2-thienyl, or 3-thienyl.

$R_2$ is hydrogen or methyl, especially hydrogen.

$R_3$ is hydrogen, sodium or potassium, especially hydrogen.

$R_4$ is

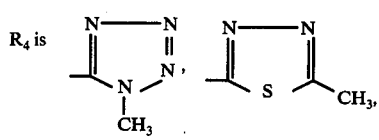

especially 5-methyl-1,3,4-thiadiazol-2-yl and 1-methyl-1H-tetrazol-5-yl.

Compounds of formula I are obtained by reacting an α-ureido compound of the formula

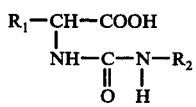

with a 3-heterothio-7-amino substituted cephalosporin of the formula

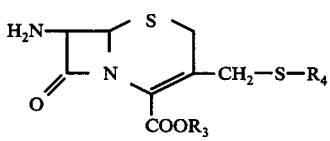

wherein $R_3$ is preferably diphenylmethyl or t-butyl or other ester protecting groups.

This reaction is carried out by converting the α-ureido compound of formula II to a mixed carbonic or other anhydride by treating a solution of the α-ureido compound in an organic solvent containing a tri(lower alkyl)amine with an anhydride forming agent, i.e. a lower alkyl chloroformate, an aryl chloroformate, or an acyl halide, at reduced temperatures of from about 0° C to about −20° C.

Alternatively, the α-ureido compound of formula II can be converted to an activated ester by reacting with a carboxyl group activating agent such as dicyclohexylcarbodiimide or bisimidazole carbonyl. In some cases the carboxyl group may be activated by conversion to an acid halide, e.g. the chloride, or to an azide.

The methods of preparing the 60-ureido compounds of formula II are known to those skilled in the art and a number of such methods are discussed in Ser. No. 93,490 referred to above.

The compounds of formula I can also be prepared by acylating the compound of formula III with an acid chloride of formula

or an α-(substituted)amino acid of the formula

wherein Y is a protecting group such as

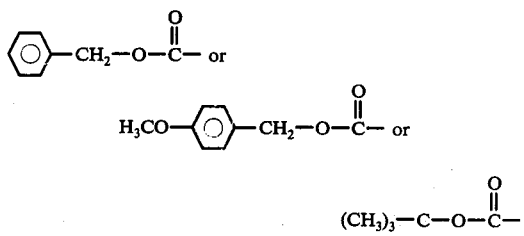

to yield after removal of the protecting group the intermediate of formula

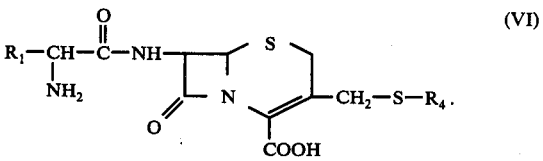

Various intermdiates of formula VI are disclosed in U.S. Pat. Nos. 3,821,207; 3,813,388; 3,641,021; 3,759,904; and 3,796,801.

The intermediates of formula VI is converted to the final products of formula I by treatment with an isocyanate of the formula

or when $R_2$ is hydrogen an alkali or alkaline earth cyanate such as potassium cyanate in solution at a pH of from about 7 to about 8.

The final products of formula I can also be prepared by reacting the compound of formula II with 7-ACA preferably in the presence of dicyclohexylcarbodiimide to yield the compound of formula VIII (as disclosed in U.S. Pat. No. 3,833,568)

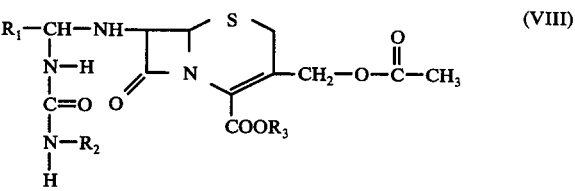

followed by treatment with the compound of formula $$R_4-S-H \quad (IX)$$

in solution at a pH of from about 7.8 to about 8.0.

Similarly, the final products of formula I can be prepared by reacting the compounds of formula IV or V with an ester of 7-ACA preferably in the presence of dicyclohexylcarbodiimide followed by treatment with an cid (HX), preferably trifluoroacetic acid in the presence of anisole, to yield the salt of formula

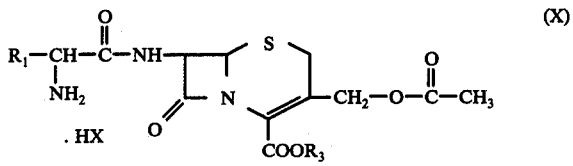

(X)

The salt of formula X is treated with the isocyanate of formula VII (or the alkali or alkaline earth cyanate where $R_2$ is hydrogen) followed by treatment with the compound of formula IX to yield the final product of formula I.

The compounds of formula I wherein $R_3$ is lower alkyl, phenyl-lower alkyl, substituted phenyl-lower alkyl, diphenyl-lower alkyl, or the acyloxymethyl group

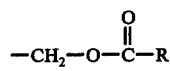

may be obtained by reacting the 3-heterothio-7-amino substituted cephalosporin of formula III or the 7-ACA either before or after the acylation of the 7-amino substituent with one or two moles of a compound of the formula

 (XI)

or

 (XII)

wherein halo is preferably chlorine or bromine in an inert solvent such as dimethylformamide, acetone, dioxane, benzene, or the like at about ambient temperature or below.

Similarly, the compounds of formula I wherein $R_3$ is tri(lower alkyl)stannyl or tri(lower alkyl)silyl are obtained by introducing such groups onto the 3-heterothio cephalosporanic acid moiety either before or after the acylation reaction.

The carboxylate salts of the compound of formula I are formed by reacting the carboxyl group of the cephalosporanic acid moiety, i.e. $R_3$ is hydrogen, with any of the salt forming ions described above.

It will be appreciated that the compounds of formula I are optically active due to the presence of an asymmetric carbon atom in the 7-position side chain. By selection of the appropriate starting material it is possible to obtain the compounds of formula I as a mixture of optically active isomers or isolated as a single isomer. The various isomers as well as their mixtures are within the scope of this invention.

The compounds of formula I have a broad spectrum of antibacterial activity against both gram positive and gram negative organisms such as *Staphylococcus aureus, Salmonella schottmuelleri, Klebsiella pneumoniae, Proteus rettgeri, Escherichia coli, Streptococcus pyogenes*, etc.

In particular, it has been found that the L-isomer of the compounds of formula I wherein $R_2$ is hydrogen are surprisingly active againt betalactamase producing organisms such as Enterobacter, indole-positive Proteus, resistant *Escherichia coli*, and Serratia.

The compounds of formula I can be used as antibacterial agents in a prophylactic manner, e.g., in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 5.0 mg./kg. in mice.

Up to about 600 mg. of a compound of formula I or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.2 to 1% by weight of such compounds admixed with, suspended or dissolved in conventional inert dry or aqueous carriers for application by washing or spraying.

They are also useful as nutritional supplements in animal feeds.

Illustrative process details are provided in the examples for the various reactions. All temperatures are on the centrigrade scale.

EXAMPLE 1

7β-[[[(Aminocarbonyl)amino](DL-2-thienyl)acetyl]-amino]-3-[[(1-methyl-1H-tetrazol-5-yl)thio]methyl]-8-oxo-5-thia-1-azabicyclo-[4.2.0]oct-2-ene-2-carboxylic acid (a) DL-α-ureido-2-thiopheneacetic acid 15.8 g. (0.1 mol.) of DL-2-thienylglycine are heated together with 8.2 g. (0.1 mol.) of potassium cyanate in 100 ml. of water. After 30 minutes, the mixture is cooled and acidified with dilute hydrochloric acid. The precipitated product, DL-α-ureido-2-thiopheneacetic acid, is filtered, washed with ice water and a small amount of ethanol. Recrystallization from methanol yields 17 g. of white crystals, of DL-α-ureido-2-thiopheneacetic acid; m.p. 183°–185°.

(b) 3-[(Acetyloxy)methyl]-7β-[[[(aminocarbonyl-)amino](DL-2-thienyl)acetyl]amino]-8-oxo-5-thia-1-azabicyclo[4.2.0]-oct-2-ene-2-carboxylic acid 9.2 g. (50 mmol.) of DL-α-ureido-2-thiopheneacetic acid from part (a) are dissolved in 40 ml. of absolute dimethylformamide. 10.3 g. (50 mmol.) of dicyclohexylcarbodiimide dissolved in 10 ml. of methylene chloride are added dropwise at 0°. After stirring for ½ hour, a solution of 13.5 g. (50 mmol.) of 7-aminocephalosporanic acid and 10 g. (100 mmol.) of triethylamine is added. This mixture is stirred for 24 hours at 5°. After filtering, the filtrate is concentrated under vacuum, the oily residue is taken up in water, filtered and after treating with activated carbon at 5° it is layered over with ethyl acetate and acidified with 2N hydrochloric acid. The ethyl acetate solution is washed with water, dried and concentrated. 8.1 g. of a viscid residue are obtained.

The product, 3-[(acetyloxy)methyl]-7β-[[[(aminocarbonyl)-amino](DL-2-thienyl)acetyl]amino]-8-oxo-5-thia-1-azabicyclo-[4.2.0]oct-2-ene-2-carboxylic acid, is recrystallized twice from isopropanol; yield 2.1 g. The intermediate of part (b) can also be obtained by the following synthesis:

(c) DL-[[[(1,1-Dimethylethoxy)carbonyl]amino]thien-2-yl]acetic acid 3.8 g. (25 mmol.) of DL-2-thienylglycine and 2 g. (50 mmol.) of magnesium oxide in 50 ml. of water/dioxane (1:1) are stirred for one hour at room temperature. 4.25 g. (28 mmol.) of t-butyloxycarbonylazide dissolved in 15 ml. of dioxane are added dropwise and the reaction mixture is stirred for 24 hours at 50°. After filtering, the filtrate is concentrated under vacuum, the oily residue is treated with ethyl acetate and then taken up with water. This is then acidified with citric acid while cooling with ice and the aqueous acid solution is extracted with ethyl acetate. The solvent is drawn off from the ethyl acetate solution to obtain 4 g. of white product, DL-[[[(1,1-dimethylethoxy)carbonyl]amino]thien-2-yl]acetic acid; m.p. 70°–72°.

(d) 3-[(Acetyloxy)methyl]-7β-[[[[(1,1-dimethylethoxy)carbonyl]amino](DL-2-thienyl)acetyl]amino]-8-oxo-5-thia-1-azabicyclo[4.2.0]oct-2-ene-2-carboxylic acid, diphenylmethyl ester 5.4 g. (20 mmol.) of DL-[[[(1,1-dimethylethoxy)carbonyl]amino]thien-2-yl]acetic acid from part (c) are dissolved in 50 ml. of tetrahydrofuran and 4.05 g. (20 mmol.) of dicyclohexylcarbodiimide are added at 0°. After stirring for 30 minutes, 8.8 g. (20 mmol.) of 7-aminocephalosporanic acid, diphenylmethyl ester are added dropwise. After 24 hours, the precipitated dicyclohexylurea is filtered off. After drawing off the solvent and recrystallizing the beige residue from methylene chloride/potassium ether 10.5 g. of the product, 3-[(acetyloxy)methyl-7β-[[[[(1,1-dimethylethoxy)carbonyl]amino](DL-2-thienyl)acetyl]amino]-8-oxo-5-thia-1-azabicyclo[4.2.0]oct-2-ene-2-carboxylic acid, diphenylmethyl ester, are obtained as a light beige powder; m.p. 78° (dec.).

(e) 3-[(Acetyloxy)methyl]-7β-≅[[[(aminocarbonyl)amino](DL-2-thienyl)acetyl]amino]-8-oxo-5-thia-1-azabicyclo[4.2.0]-oct-2-ene-2-carboxylic acid 5 g. of 3-[(acetyloxy)methyl]-7β-[[[[(1,1-dimethylethoxy)carbonyl]amino](DL-2-thienyl)acetyl]amino]-8-oxo-5-thia-1-azabicyclo[4.2.0]oct-2-ene-2-carboxylic acid, diphenylmethyl ester from part (d) are stirred for 15 minutes in a mixture of 20 ml. of trifluoroacetic acid and 3 ml. of anisole at 5°. After evaporating the trifluoroacetic acid under vacuum and washing the residue with ether, 2.3 g. of 3-[(acetyloxy)methyl]-7β-[[(α-amino-DL-2-thienyl)acetyl]amino]-8-oxo-5-thia-1-azabicyclo[4.2.0]oct-2-ene-2-carboxylic acid, trifluoroacetic acid salt are obtained. This product is dissolved in water and the solution is adjusted to pH 8 with sodium hydroxide. It is then quickly heated to 80° and 0.4 g. of potassium cyanate dissolved in 2 ml. of water are added. After stirring for 1 minute, the reaction mixture is quickly cooled, layered over with ethyl acetate and acidified to pH 3.5 with 2N hydrochloric acid. This is extracted with 5 × 100 ml. of ethyl acetate. The combined ethyl acetate extracts are dried, concentrated to about ⅓ the volume, treated with activated carbon and the product, 3-[(acetyloxy)methyl]-7β-[[[(aminocarbonyl)amino](DL-2-thienyl)acetyl]amino]-8-oxo-5-thia-1-azabicyclo[4.2.0]oct-2-ene-2-carboxylic acid, is precipitated with petroleum ether. The product is crystallized from isopropanol as light beige crystals; m.p. 145° (dec.).

(f) 7β-[[[(Aminocarbonyl)amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid 2.27 g. of the 3-[(acetyloxy)methyl]-7β-[[[(aminocarbonyl)amino](DL-2-thienyl)acetyl]amino]-8-oxo-5-thia-1-azabicyclo[4.2.0]oct-2-ene-2-carboxylic acid from part (b) or (e) are dissolved in a mixture of acetone/water (1:1) with the aid of 5N sodium hydroxide. The pH is adjusted to 7.6–8.0 and 5 mmol. of 1-methyl-1H-tetrazole-5-thiol is added. The pH is maintained at 7.8 by the addition of 5N sodium hydroxide. The reaction mixture is heated for 3 hours at 50°–60°. After cooling and distilling off the acetone, the mixture is acidified to pH 2.5 with 2N hydrochloric acid while cooling with ice and the precipitate is extracted with ethyl acetate to yield the titled product.

EXAMPLE 2

7β-[[[(Aminocarbonyl)amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid (a) DL-α-[[[(4-Methoxyphenyl)methoxy]carbonyl]amino]-2-thiopheneacetic acid 1.9 g. (12.5 mmol.) of DL-2-thienylglycine and 1 g. of magnesium oxide are suspended in 50 mmol. of water. After stirring for ½ hour, 3 g. (15 mmol.) of (p-methoxybenzyloxycarbonyl)azide in 25 ml. of dioxane are added. After stirring for 48 hours at room temperature, the mixture is filtered. The filtrate is extracted with 200 ml. of ether. The aqueous phase is layered over with an equal volume of ethyl acetate and vigorously stirred with 20 g. of ion exchange resin (Dowex 50, acid form) for 2 hours. The ethyl acetate is separated, washed with 100 ml. of water, dried and concentrated. A light oil remains as residue which crystallizes on trituration with petroleum ether. The DL-α-[[[(4-methoxyphenyl)methoxy]carbonyl]amino]-2-thiopheneacetic acid obtained melts at 153°–156°.

(b) DL-α-[[[(4-Methoxyphenyl)methoxy]carbonyl]amino]-2-thiopheneacetic acid, 2,5-dioxo-1-pyrrolidinyl ester 6.7 g. (20 mmol.) of the DL-α-[[[(4-methoxyphenyl)methoxy]carbonyl]amino]-2-thiopheneacetic acid from part (a) are dissolved in 150 ml. of tetrahydrofuran. 2.3 g. of N hydroxysuccinnamide and 4.1 g. (20 mmol.) of dicyclohexylcarbodiimide in tetrahydrofuran are added dropwise at 0°. After stirring for 24 hours, the mixture is filtered and the filtrate is concentrated. The oily residue crystallizes on rubbing. Upon recrystallization from benzene/cyclohexane, 7.5 g. of light beige crystalline DL-α-[[[(4-methoxyphenyl)methoxy]carbonyl]amino]-2-thiopheneacetic acid, 2,5-dioxo-1-pyrrolidinyl ester; m.p. 140°–142°, are obtained.

(c) 7β-[[[[[(4-Methoxyphenyl)methoxy]carbonyl]amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid and 7β-[[[[[(4-Methoxyphenyl)methoxy]carbonyl]amino](DL-2-thienyl)acetyl]amino]-3-[[(1-methyl-1H-tetrazol-5-yl)thio]methyl]-8-oxo-5-thia-1-azabicyclo[4.2.0]-oct-2-ene-2-carboxylic acid, diphenylmethyl ester 3.2 g. (10 mmol.) of 3-[(1-methyl-1H-tetrazol-5-yl)thio]-7-aminocephalosporanic acid are dissolved in 20 ml.

of dimethylformamide by the addition of 2.02 g. (20 mmol.) of triethylamine. 4.18 g. (10 mmol.) of DL-α-[[[(4-methoxyphenyl)methoxy]carbonyl]amino]-2-thiopheneacetic acid, 2,5-dioxo-1-pyrrolidinyl ester from part (b) are added dropwise at room temperature. After three hours, the solvent is distilled off under oil vacuum. There remains a brown viscid residue which is completely soluble in water with the aid of a little sodium carbonate. The aqueous solution is shaken with ethyl acetate, the aqueous phase is treated with activated carbon, layered over with ethyl acetate and acidified with 2N hydrochloric acid. The solvent is drawn off from the ethyl acetate extract and the residue is recrystallized from methylene chloride/petroleum ether to obtain 2.5 g. of 7β-[[[[[(4-methoxyphenyl)methoxy]carbonyl]amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 63° (dec.).

Similarly, by employing an equivalent amount of the diphenylmethyl ester of 3-[(1-methyl-1H-tetrazol-5-yl)thio]-7-aminocephalosporanic acid, m.p. 168°-169° (dec.)., in the above procedure one obtains as a beige powder 7β-[[[[[(4-methoxyphenyl)methoxy]carbonyl]amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester; m.p. 98°-100° (dec.).

(d) 7β-[[[(Aminocarbonyl)amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid 1.2 g. (2.5 mmol.) of the 7β-[[[[[(4-methoxyphenyl)methoxy]carbonyl]amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid from part (c) or an equivalent amount of the diphenylmethyl ester are treated at 5° with a mixture of trifluoroacetic acid and 1.5 ml. of anisole. The solvent is drawn off and the solid residue is washed with ether to obtain 0.7 g. of 7β-[[(α-amino-DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid trifluoroacetic acid salt. This crude salt is converted with potassium cyanate to the ureido compound by the procedure of example 1(e).

The ureido compound is crystallized from isopropanol and recrystallized once for tetrahydrofuran/petroleum ether. The product, 7β-[[[(aminocarbonyl)amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, is obtained as a beige powder; m.p. 165°-167° (dec.).

EXAMPLE 3

7β-[[[(Aminocarbonyl)amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt An equimolar aqueous solution of the final product from either example 1 or 2 and potassium bicarbonate is freeze-dried to yield as a light powder 7β-[[[(aminocarbonyl)amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt; m.p. 183°-186°.

Similarly, by employing sodium bicarbonate one obtains the sodium salt.

EXAMPLE 4

7β-[[[(Aminocarbonyl)amino](DL-2-thienyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid (a) 7-Amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester 18 g. of 7-amino-3-[[(5-methyl-1,3,4-thiadiazol-5-yl)thio]methyl]-8-oxo-5-thia-1-azabicyclo[4.2.0]oct-2-ene-2-carboxylic acid are suspended in 350 ml. of tetrahydrofuran. 4.1 ml. of 70% perchloric acid are added dropwise. After 30 minutes, a slightly turbid solution forms. This solution is filtered and to the filtrate is added dropwise with stirring 12 g. of diphenyldiazomethane and 20 ml. of tetrahydrofuran. After 3 hours, the reaction mixture is poured into 2 liters of absolute ether. The solid, light brown precipitate, which is the perchloric acid salt of the desired product, is dried over Kieselgel in a desiccator. To obtain the base, the perchloric acid salt is dissolved in water and treated with the calculated equivalent of potassium bicarbonate. The aqueous solution obtained is extracted with chloroform. The chloroform phase is treated with activated carbon and sodium sulfate to obtain 10 g. of the product, 7-amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester, as a light brown powder, m.p. 157°-159°. The product is recrystallized from tetrahydrofuran/petroleum ether.

(b) 7β-[[[[[(4-Methoxyphenyl)methoxy]carbonyl]amino](DL-2-thienyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester 8.8 g. of the diphenylmethyl ester from part (a), 5.77 g. of DL-α-[[[(4-methoxyphenyl)methoxy]carbonyl]amino]-2-thiopheneacetic acid from example 2(a) and 3.55 g. of dicyclohexylcarbodiimide in 80 ml. of tetrahydrofuran are stirred for 24 hours at 0°. The tetrahydrofuran is drawn off under vacuum and the product is obtained from the filtrate by recrystallization from tetrahydrofuran/petroleum ether. Beige crystals of 7β-[[[[(4-methoxyphenyl)methoxy]carbonyl]amino](DL-2-thienyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester; m.p. 104°-106°, are obtained.

(c) 7$^b$-[[[(Aminocarbonyl)amino](DL-2-thienyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid The product from part (b) is treated with trifluoroacetic acid and anisole at 0° C followed by treatment at 80° with potassium cyanate at pH 7.8 according to the procedure of example 1(e). The 7β-[[[(aminocarbonyl)amino](DL-2-thienyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid obtained is recrystallized from tetrahydrofuran/petroleum ether as a beige powder, m.p. 155°-157° (dec.).

EXAMPLE 5

7β-[[[(Aminocarbonyl)amino](DL-2-thienyl)acetyl]-amino]-3-[[(5-methyl-1,3,4-thiadiazol-2-yl)thio]methyl]-8-oxo-5-thia-1-azabicyclo[4.2.0]oct-2-ene-2-carboxylic acid, potassium salt An equimolar aqueous solution of the final product from example 4 and potassium bicarbonate is freeze-dried to yield as a beige powder 7β-[[[(aminocarbonyl)amino](DL-2-thienyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid, potassium salt; m.p. 194°–196° (dec.).

EXAMPLE 6

7β-[[[(Aminocarbonyl)amino](DL-3-thienyl)acetyl]-amino]-3-[[(1-methyl-1H-tetrazol-5-yl)thio]methyl]-8-oxo-5-thia-1-azabicyclo[4.2.0]oct-2-ene-2-carboxylic acid (a) DL-α-Bromo-3-thiopheneacetic acid 3-thienylbromide is treated with butyl lithium and chloral to obtain 3-[(1-hydroxy-2-trichloro)ethyl]thiophene which is then treated with sodium methoxide to obtain α-methoxy-3-thienylacetic acid [Gronowitz et al., Ark. Chemi., 17, 561 (1961)].

150 ml. of 30% hydrogen bromide in acetic acid is added to a solution of 16 g. (100 mmol.) of (α-methoxy-3-thienyl)acetic acid in 50 ml. of glacial acetic acid. The mixture is left to stand at room temperature for 24 hours and then poured into ice water. The solution is extracted three times with 60 ml. of ether. The ether phase is washed with water, dried over magnesium sulfate and evaporated. The residue, 18 g. of crude DL-α-bromo-3-thiopheneacetic acid are recrystallized from cyclohexane; yield 14 g.; m.p. 80°–82°.

(b) DL-α-Azido-3-thiopheneacetic acid 4 g. (62 mmol.) of sodium azide and 3.5 g. (33 mmol.) of sodium carbonate are added to a solution of 12 g. (54 mmol.) of DL-α-bromo-3-thiopheneacetic acid in 75 ml. of acetone (96%). The mixture is stirred at room temperature for 12 hours in darkness and after this time the solvent is evaporated and the residue is dissolved in 75 ml. of water. 50 ml. of ether is added, the water phase is acidified with 2N sulfuric acid and extracted quickly twice more with 50 ml. of ether. After washing with water and drying over sodium sulfate, the combined ether phases are evaporated. Crystallization of the residue from cyclohexane yields 7.4 g. of white crystalline DL-α-azido-3-thiopheneacetic acid; m.p. 58°–59°.

(c) DL-α-Amino-3-thiopheneacetic acid 0.3 g. of palladium/barium sulfate catalyst are added to a solution of 6 g. of DL-α-azido-3-thiopheneacetic acid in 40 ml. of ethanol and 40 ml. of 0.5N hydrochloric acid. Hydrogenation takes place at about 60 psig. after 2 hours. After filtration, the volume is concentrated to about 30 ml. When the pH is brought to 6.5 with ammonia, the amino acid separates as a white powder. After washing with ethanol/water and drying, 3.5 g. of the product, DL-α-amino-3-thiopheneacetic acid, are obtained; m.p. 283°–285°.

(d) DL-α-[[[(4-Methoxyphenyl)methoxy]carbonyl]-amino]-3-thiopheneacetic acid 1.9 g. (12.5 mmol.) of DL-α-amino-3-thiopheneacetic acid and 1 g. of magnesium oxide are stirred in 25 ml. of water and 25 ml. of dioxane. After stirring for 1 hour, 3.0 g. (15 mmol.) of [(p-methoxybenzyl)oxy]carbonylazide are added. Stirring is continued for 24 hours. The mixture is filtered and extracted with 20 ml. of ether. 50 ml. of ethyl acetate and 20 g. of Dowex 50 (H+ form) are added to the filtrate and the mixture is stirred well for two hours. The ethyl acetate phase is separated, washed with 50 ml. of water, dried over sodium sulfate and evaporated. The oily residue crystallizes after the addition of pentane to yield 3.4 g. of white crystalline DL-α[[[(4-methoxyphenyl)methoxy]carbonyl]amino]-3-thiopheneacetic acid; m.p. 118° (dec.).

(e) 3-[(Acetyloxy)methyl-7β-[[[(aminocarbonyl)amino](DL-3-thienyl)acetyl]amino]-8-oxo-5-thia-1-azabicyclo[4.2.0]oct-2-ene-2-carboxylic acid 5 g. of the product from part (d), 1.5 g. of triethylamine and 1.8 g. of chloroformic acid ethyl ester in 50 ml. of tetrahydrofuran are converted to the mixed anhydride. The mixed anhydride is reacted with a solution of 4 g. of 7-aminocephalosporanic acid and 2.5 g. of triethylamine in methylene chloride for 12 hours. The solvent is then removed from the solution and the partially solid residue is dissolved with water and a small amount of sodium carbonate and extracted with 50 ml. of ethyl acetate. The aqueous phase is cooled, acidified to pH 2.5 with 2N hydrochloric acid and extracted with ethyl acetate. The organic phase is treated with activated carbon and concentrated to obtain 3.7 g. of light beige 3-[(acetyloxy)methyl]-7β-[[[[(4-methoxyphenyl)methoxy]carbonyl]amino](DL-3-thienyl)acetyl]amino]-8-oxo-5-thia-1-azabicyclo [4.2.0]oct-2-ene-2-carboxylic acid; m.p. 113° (dec.), which is recrystallized from methylene chloride/petroleum ether. The α-amino protecting group is removed and the resultiing compound is treated with potassium cyanate as in example 2(d) to yield the titled compound.

(f) 7ᵇ-[[[(Aminocarbonyl)amino](DL-3-thienyl) acetyl]amino]-3-[[(1-methyl-1H-tetrazol-5-yl)thio]methyl]-8-oxo-5-thia-1-azabicyclo[4.2.0]-oct-2-ene-2-carboxylic acid The 3-[(acetyloxy)methyl]-7β-[[[(aminocarbonyl)amino](DL-3-thienyl)acetyl]amino]-8-oxo-5-thia-1-azabicyclo[4.2.0]]oct-2-ene-2-carboxylic acid from part (e) is treated with 1-methyl-1H-tetrazole-5-thiol according to the procedure of example 1(f) to yield the titled compound.

The 7ᵇ-[[[(aminocarbonyl)amino](DL-3-thienyl) acetyl]amino]-3-[[(1-methyl-1H-tetrazol-5-yl)thio]methyl]-8-oxo-5-thia-1-azabicyclo[4.2.0]oct-2-ene-2-carboxylic acid can also be obtained by following the procedure of example 2 but substituting DL-3-thienylglycine for the DL-2-thienylglycine in part (a) of example 2.

Following the procedure of example 3, one can obtain the sodium and potassium salts.

EXAMPLE 7

7β-[[[(Aminocarbonyl)amino](D-2-thienyl)acetyl]-amino]-3-[[(1-methyl-1H-tetrazol-5-yl)thio]methyl]-8-oxo-5-thia-1-azabicyclo[4.2.0]oct-2-ene-2-carboxylic acid (a) D-α-[[[(4-Methoxyphenyl)methoxy]carbonyl]-amino]-2-thiopheneacetic acid 15.7 g. of D-(2-thienyl)glycine (m.p. 218°–219°, produced from the racemate with D-camphor-10-sulfonic acid) and 8 g. of magnesium oxide are suspended in 200 ml. of water. To this suspension is added a solution of 22.8 g. of (p-methoxyphenyl)methoxycarbonylazide in 200 ml. of dioxane and this mixture is stirred for 3 days at room temperature. The mixture is filtered, the filtrate is extracted once with ether, the aqueous phase is layered over with ethyl acetate, cooled to about 10° and acidified to pH 2 with dilute hydrochloric acid. The aqueous phase is once more extracted with ethyl acetate, the combined extracts are washed once with water, dried with magnesium sulfate and concentrated. The residue crystallizes upon trituration with petroleum ether. The crude product, D-α-[[[(4-methoxyphenyl)methoxy]carbonyl]amino]-2-thiopheneacetic acid, is recrystallized from ethyl acetate/petroleum ether, yield 25.2 g., m.p. 65°-67°.

(b) 3-[(Acetyloxy)methyl]-7β-[[[[(4-methoxyphenyl)methoxy]carbonyl]amino](D-2-thienyl)acetyl]amino]-8-oxo-5-thia-1-azabicyclo [4.2.0]oct-2-ene-2-carboxylic acid 3.2 g. (0.01 mol. ) of the product from part (a) is brought into solution in 40 ml. of methylene chloride with 1.1 ml. of N-methylmorpholine. The solution is cooled to −15°, 1.39 ml. of isobutylchloroformate are added, and the mixture is stirred for 10 minutes. To this is added a solution of 3.26 g. (0.1012 mol.) of 7-aminocephalogsporanic acid and 3.1 ml. of triethylamine in 40 ml. of methylene chloride. The mixture is stirred for 1 hour at −5° and 1 hour at 5°. This mixture is then evaporated to dryness in a rotary evaporator. The solid residue is triturated with ether and filtered under suction. The substance is then dissolved in ice water, layered over with ethyl acetate and acidified to pH 2.5. The layers are separated, the aqueous layer is extracted once more with ethyl acetate, the combined ethyl acetate extracts are washed with water, dried with magnesium sulfate and concentrated. The residue (4.9 g.) is dissolved in 200 ml. of ethyl acetate and the solution is treated with activated carbon. After filtration 2 g. of 3-[(acetyloxy)methyl]-7β-[[[[(4-methoxyphenyl)methoxy]carbonyl]amino](D-2-thienyl)acetyl]amino]-8-oxo-5-thia-1-azabicyclo[4.2.0]oct-2-ene-2-carboxylic acid, crystallize; m.p. 142°-143° (dec.).

(c) 3-[(Acetyloxy)methyl]-7β-[[(α-amino-D-2-thienyl)acetyl]amino]-8-oxo-5-thia-1-azabicyclo[4.2.0-]oct-2-ene-2-carboxylic acid 2.0 g. of the product from part (b) are added at −5° to a mixture of 10 ml. of trifluoroacetic acid and 4 ml. of anisole. The mixture is stirred for 10 minutes and is then concentrated in a rotary evaporator. The residue is treated with ether and filtered under suction. The crude 3-[(acetyloxy)methyl]-7β-[[(α-amino-D-2-thienyl)acetyl]amino]-8-oxo-5-thia-1-azabicyclo[4.2.0]oct-2-ene-2-carboxylic acid, trifluoroacetic acid salt is dissolved in 50 ml. of water and 20 ml. of a solution of the acetate form of the ion exchange resin Amberlite LA 1 in isobutylmethylketone are added. The mixture is stirred for 2 hours at room temperature. The layers are separated, the aqueous phase is washed several times with ether and freeze-dried to yield 1 g. of 3-[(acetyloxy)methyl]-7β-[[(α-amino-D-2-thienyl)acetyl]amino]-8-oxo-5-thia-1-azabicyclo[4.2.0]oct-2-ene-2-carboxylic acid.

(d) 3-[(Acetyloxy)methyl]-7β-[[[(aminocarbonyl)amino](D)-2-thienyl)acetyl]amino]-8-oxo-5-thia-1-azabicyclo[4.2.0]oct-2-ene-2-carboxylic acid A mixture of 1 g. of the product from part (c) and 0.194 g. of potassium cyanate in 7.5 ml. of water are quickly heated in a preheated bath at 80°. The mixture is then immediately cooled to room temperature and permitted to stand overnight. The reaction mixture is concentrated to about 4 ml. and the pH is adjusted to 1.5 with 2N hydrochloric acid. The precipitate is filtered under suction to obtain 0.5 g. of 3-[(acetyloxy)methyl]-7β-[[[(aminocarbonyl)amino(D-2-thienyl)acetyl]amino]-8-oxo-5-thia-1-azabicyclo[4.2.0]oct-2-ene-2-carboxylic acid; m.p. 155°-160° (dec.).

(e) 7$^b$-[[[(Aminocarbonyl)amino](DL-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid 0.01 mol. of the product from part (d) and 0.011 mol. of 1-methyl-1H-tetrazole-5-thiol are heated in an aqueous acetone solution at pH 7 according to the procedure of example 1(f) to yield the 7$^a$-[[[(aminocarbonyl)amino](D)-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid.

Following the procedure of example 3, one can obtain the sodium and potassium salts.

EXAMPLE 8

7β-[[[(Methylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid (a) 3-[(Acetyloxy)methyl]-7β-[[[(methylaminocarbonyl)amino](D-2-thienyl)acetyl]amino]-8-oxo-5-thia-1-azabicyclo[4.2.0]oct-2-ene-2-carboxylic acid 1.5 g. of 3-[(acetyloxy)methyl]-7β-[[(α-amino-D-2-thienyl)acetyl]amino]-8-oxo-5-thia-1-azabicyclo[4.2.0-]oct-2-ene-2-carboxylic acid, trifluoroacetic acid salt from example 7(c) and 1.01 ml. of triethylamine are dissolved at 0°-5° in 20 ml. of anhydrous methylene chloride. To the clear solution is added 2.49 g. of a 10% solution of methylisocyanate in methylene chloride. This mixture is stirred for 2 hours at 0°-5° and then concentrated. The residue is taken up in a little water, shaken with ether, filtered and acidified with 2N hydrochloric acid. 0.8 g. of 3-[(acetyloxy)methyl]-7β-[[[(methylaminocarbonyl)amino](D-2-thienyl)acetyl]amino]-8-oxo-5-thia-1-azabicyclo[4.2.0]oct-2-ene-2-carboxylic acid are obtained; m.p. 178°-180° (dec.).

(b)7β-[[[(Methylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid 0.01 mol. of the product from part (a) and 0.011 mol. of 1-methyl-1H-tetrazole-5-thiol are reacted according to the procedure of example 1(f) to yield the 7β-[[[(methylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid.

Following the procedure of example 3, one can obtain the sodium and potassium salts.

EXAMPLE 9

7β-[[[(Aminocarbonyl)amino](DL-3-pyridyl)acetyl]amino]-3-[[(1-methyl-1H-tetrazol-5-yl)thio]methyl]-8-oxo-5-thia-1-azabicyclo[4.2.0]oct-2-ene-2-carboxylic acid (a) DL-α-[[[(4-Methoxyphenyl)methoxy]carbonyl]amino]-3-pyridineacetic acid DL-2-(3-Pyridyl)glycine (prepared from pyridine-3-aldehyde by the Strecker synthesis) is reacted with (p-methoxybenzyloxycarbonyl)azide according to the procedure set forth in Example 2(a) to yield DL-α-[[[(4-methoxyphenyl)methoxy]carbonyl]amino]-3-pyridineacetic acid; m.p. 155°-156° (dec.).

(b) 3-[(Acetyloxy)methyl]-7β-[[[[[(4-methoxyphenyl)methoxy]carbonyl]amino](DL-3-pyridyl)acetyl]amino]-8-oxo-5-thia-1-azabicyclo[4.2.0]oct-2-ene-2-carboxylic acid The product from part (a) is reacted with isobutylchloroformate in the presence of N-methylmorpholine followed by reaction with 7-aminocephalosporanic acid according to the procedure of example 7(b) to yield the 3-[(acetyloxy)methyl]-7β-[[[[[(4-methoxyphenyl)methoxy]carbonyl]amino](DL-3-pyridyl)acetyl]amino]-8-oxo-5-thia-1-azabicyclo[4.2.0]oct-2-ene-2-carboxylic acid.

(c) 3-[(Acetyloxy)methyl]-7β-[[(α-amino-DL-3-pyridyl)acetyl]amino]-8-oxo-5-thia-1-azabicyclo[4.2.0]oct-2-ene-2-carboxylic acid, trifluoroacetic acid salt 4 g. of the product from part (b) are added at −5° to a mixture of 50 ml. of trifluoroacetic acid and 20 ml. of anisole. After 10 minutes, the trifluoroacetic acid is evaporated under vacuum. The residue is treated with ether and filtered to yield the 3-[(acetyloxy)methyl]-7β-[[(α-amino-DL-3-pyridyl)acetyl]amino]-8-oxo-5-thia-1-azabicyclo[4.2.0]oct-2-ene-2-carboxylic acid, trifluoroacetic acid salt; m.p. 138°-140° (dec.).

(d) 3-[(Acetyloxy)methyl]-7β-[[[(aminocarbonyl)amino](DL-3-pyridyl)acetyl]amino]-8-oxo-5-thia-1-azabicyclo[4.2.0]oct-2-ene-2-carboxylic acid 3.5 g. of the product from part (c) and 1.09 g. of potassium cyanate are stirred overnight in 50 ml. of water at room temperature. The reaction mixture is filtered and the filtrate is freeze-dried to yield the 3-[(acetyloxy)methyl]-7β-[[[(aminocarbonyl)amino](DL-3-pyridyl)acetyl]amino]-8-oxo-5-thia-1-azabicyclo[4.2.0]oct-2-ene-2-carboxylic acid.

(e) 7β-[[[(Aminocarbonyl)amino](DL-3-pyridyl)acetyl]amino]-3-[[(1-methyl-1H-tetrazol-5-yl)thio]methyl]-8-oxo-5-thia-1-azabicyclo[4.2.0]oct-2-ene-2-carboxylic acid The product from part (d) and 1-methyl-1H-tetrazole-5-thiol are reacted according to the procedure of example 1(f) to yield the 7β-[[[(aminocarbonyl)amino](DL-3-pyridyl)acetyl]amino]-3-[[(1-methyl-1H-tetrazol-5-yl)thio]methyl]-8-oxo-5-thia-1-azabicyclo[4.2.0]oct-2-ene-2-carboxylic acid.

EXAMPLE 10

7β-[[[(Aminocarbonyl)amino](L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid (a) L-α-[[[(4-Methoxyphenyl)methoxy]carbonyl]amino]-2-thiopheneacetic acid 14.2 g. of L-(2-thienyl)glycine (prepared by the method of Nishimura et al., Nippon Kagaku Zasshi, Vol. 82, p. 1688-91 (1961); Chem. Abst., Vol. 58, p. 11464f) are suspended in 142 ml. of water and brought into solution by the addition of 37.9 ml. of triethylamine. A solution of 20.6 g. of (p-methoxyphenyl)methoxycarbonylazide in 142 ml. of dioxane are added with stirring. The mixture which is turbid at first becomes clear after 30 minutes. This is stirred for an additional hour at room temperature. The dioxane is then evaporated in vacuum. Flakes form in the aqueous phase which are extracted by shaking with ether. The aqueous phase is cooled to 0°, layered over with ethyl acetate and acidified with 2N hydrochloric acid to pH 2.5. The aqueous phase is extracted twice more with ethyl acetate, the combined ethyl acetate extracts are dried with magnesium sulfate and concentrated in vacuum to 23.5 g. of L-α-[[[(4-methoxyphenyl)methoxy]carbonyl]amino]-2-thiopheneacetic acid; m.p. 100°-102°; [α]$_D^{20}$ = +68.3° (c=1, tetrahydrofuran).

(b) 7β-[[[[[(4-Methoxyphenyl)methoxy]carbonyl]amino](L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 14.9 g. of 3-[(1-methyl-1H-tetrazol-5-yl)thio]-7-aminocephalosporanic acid, diphenylmethyl ester are dissolved in 300 ml. of methylene chloride and 300 ml. of anhydrous tetrahydrofuran are added. Then 11.62 g. of L-α-[[[(4-methoxyphenyl)methoxy]carbonyl]amino]-2-thiopheneacetic acid from part (a) are added, the mixture is cooled to 0°, and a solution of 6.79 g. of dicyclohexylcarbodiimide in 100 ml. of anhydrous tetrahydrofuran is added dropwise with stirring over 30 minutes. The reaction mixture is stirred for 90 minutes at 0°-5° and 90 minutes at room temperature. The precipitated dicyclohexylurea is then filtered off and the filtrate is concentrated in vacuum. The residue is taken up with ethyl acetate, filtered, washed with sodium bicarbonate solution and with water. The ethyl acetate solution is dried with magnesium sulfate, treated with activated charcoal, filtered and concentrated in vacuum to a small volume. On stirring in excess petroleum ether, 24 g. of 7α-[[[[[(4-methoxyphenyl)methoxy]carbonyl]amino](L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester; m.p. 110°; are obtained as a precipitate.

(c) 7β-[[(α-Amino-L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt 24 g. of the diphenylmethyl ester product from part (b) are stirred in 100 ml. of anisole and 300 ml. of trifluoroacetic acid are added dropwise at 0°. After 10 minutes, this mixture is evaporated under vacuum. The residue is treated with ether and filtered to yield 17.8 g. of 7β-[[(α-amino-L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt.

(d) 7β-[[[(Aminocarbonyl)amino](L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid 12 g. of the trifluoroacetic acid salt product from part (c) are added to a solution of 3.4 g. of potassium cyanate in 85 ml. of water and stirred for 3 hours at room temperature. This mixture is filtered and the filtrate is acidified to pH 1.5 with 2N hydrochloric acid while cooling. The precipitate is isolated and yields 6.8 g. of 7β-[[[(aminocarbonyl)amino](L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 149°-153° (dec.).

An aqueous equimolar solution of this acid and sodium bicarbonate is lyophilized to yield 7β-[[[(aminocarbonyl)amino](L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt; m.p. 187°-188° (dec.). In a similar manner, one can obtain the potassium salt.

EXAMPLE 11

7β-[[[(Aminocarbonyl)amino](L-3-thienyl)acetyl]-amino]-3-[[(1-methyl-1H-tetrazol-5-yl)thio]methyl]-8-oxo-5-thia-1-azabicyclo[4.2.0]oct-2-ene-2-carboxylic acid (a) L-α-[[[(4-Methoxyphenyl)methoxy]carbonyl]-amino]-3-thiopheneacetic acid 18 g. of L-(3-thienyl)glycine (prepared by the method of Nishimura et al., supra) are suspended in 300 ml. of water with 10 g. of magnesium oxide. 32 g. of (p-methoxyphenyl)methoxycarbonylazide in 250 ml. of dioxane are added dropwise. The mixture is stirred for 24 hours at room temperature, then the dioxane is distilled off, filtered and the filtrate is extracted by shaking with ether. The aqueous phase is layered with ethyl acetate and acidified to pH 2.5 with 2N hydrochloric acid with cooling. The ethyl acetate is washed with water, dried over sodium sulfate and evaporated. The residual oil is dissolved in toluene, cyclohexane is added, and the mixture is refrigerated. Crystallization begins and 20.8 g. of white crystalline L-α-[[[(4-methoxyphenyl)methoxy]carbonyl]amino]-3-thiopheneacetic acid are obtained; m.p. 95°–97°; $[α]_D^{25} = +76.8°$ (0.1% in methanol).

(b) 7β-[[[[[(4-Methoxyphenyl)methoxy]carbonyl]-amino](L-3-thienyl)acetyl]amino]-3-[[(1-methyl-1H-tetrazol-5-yl)thio]methyl]-8-oxo-5-thia-1-azabicyclo[4.2.0-]oct-2-ene-2-carboxylic acid, diphenylmethyl ester 10 g. of the L-α-[[[(4-methoxyphenyl)methoxy]carbonyl]amino]-3-thiopheneacetic acid from part (a) are dissolved in 150 ml. of tetrahydrofuran and stirred for 15 minutes at 0° with 6.5 g. of dicyclohexylcarbodiimide. Then 14 g. of 3-[(1-methyl-1H-tetrazol-5-yl)thio]-7-aminocephalosporanic acid, diphenylmethyl ester dissolved in 100 ml. of tetrahydrofuran are added. After 12 hours, the reaction mixture is filtered, the filtrate is treated with charcoal and evaporated in vacuum. The residual brown oil is dissolved in 20 ml. of methylene chloride and added dropwise to a mixture of ether and petroleum ether. 20 g. of light yellow 7β-[[[[[(4-methoxyphenyl)methoxy]carbonyl]amino](L-3-thienyl)acetyl]-amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester are obtained; m.p. 95°.

(c) 7β-[[(α-Amino-L-3-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt 13 g. of the diphenylmethyl ester product from part (b) are dissolved in 200 ml. of anisole-trifluoroacetic acid (1:4) at 5°. After 10 minutes stirring, the mixture is evaporated under vacuum. The residue is treated with a mixture of ether and petroleum ether and filtered to yield 8.4 g. of solid yellow 7β-[[(α-amino-L-3-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt; m.p. 125° (dec.).

(d) 7β-[[[(Aminocarbonyl)amino](L-3-thienyl-)acetyl]amino]-3-[[(1-methyl-1H-tetrazol-5-yl)thio]methyl]-8-oxo-5-thia-1-azabicyclo[4.2.0]oct-2-ene-2-carboxylic acid 7.9 g. of the trifluoroacetic acid salt product from part (c) are dissolved in 50 ml. of water and the pH is adjusted to 7.2 with 2N sodium hydroxide. After the addition of 1.5 g. of potassium cyanate, the mixture is stirred for 3 hours at constant pH. The reaction mixture is cooled, adjusted to pH 1.5 with 2N hydrochloric acid, the precipitate is filtered off and dissolved in methanol, then treated with charcoal. Concentrating the methanolic solution crystallizes 4.2 g. of 7β-[[[(aminocarbonyl)amino](L-3-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 157° (dec.).

An equimolar solution of this acid and potassium bicarbonate is lyophilized to obtain as a yellow powder 7β-[[[(aminocarbonyl)amino](L-3-thienyl)acetyl]-amino]-3-[[(1-methyl-1H-tetrazol-5-yl)thio]methyl]-8-oxo-5-thia-1-azabicyclo[4.2.0]oct-2-ene-2-carboxylic acid, potassium salt; m.p. 174° (dec.). In a similar manner, by employing sodium bicarbonate, one obtains the sodium salt.

In an analogous manner, by substituting D-(3-thienyl)glycine for the L-isomer in part (a) and then following the procedure of example 11, one obtains 7β-[[[(aminocarbonyl)amino](D-3-thienyl)acetyl]-amino]-3-[[(1-methyl-1H-tetrazol-5-yl)thio]methyl]-8-oxo-5-thia-1-azabicyclo[4.2.0]oct-2-ene-2-carboxylic acid and its sodium and potassium salts.

EXAMPLES 12–31

Following the procedures of any of examples 1, 2, 6, or 9 but substituting for the DL-2-thienylglycine, DL-3-thienylglycine, and DL-3-pyridylglycine one of the following:

DL-2-furylglycine
DL-3-furylglycine
DL-2-pyrrylglycine
DL-3-pyrrylglycine
DL-2-pyridylglycine
DL-4-pyridylglycine
DL-2-thiazolylglycine
DL-5-thiazolylglycine
DL-3-isothiazolylglycine
DL-5-isothiazolylglycine
DL-2-oxazolylglycine
DL-5-oxazolylglycine
DL-3-isoxazolylglycine
DL-5-isoxazolylglycine
DL-3-(1,2,4-thiadiazolyl)glycine
DL-5-(1,2,4-thiadiazolyl)glycine
DL-5-(1-methyltetrazolyl)glycine
DL-2-(5-chlorothienyl)glycine
DL-3-(4-methylthienyl)glycine
DL-2-(4-chloropyrryl)glycine one obtains 7β-[[[(aminocarbonyl)amino](DL-2-furyl)acetyl]-amino]-3-[[(1-methyl-1H-tetrazol-5-yl)thio]methyl]-8-oxo-5-thia-1-azabicyclo[4.2.0]oct-2-ene2-carboxylic acid;

7β-[[[(aminocarbonyl)amino](DL-3-furyl)acetyl]-amino]-3-[[(1methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-2-pyrryl)acetyl]-amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-3-pyrryl)acetyl]-amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-2-pyridyl)acetyl]-amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-4-pyridyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-2-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-5-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-3-isothiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-5-isothiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-2-oxazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-5-oxazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-3-isoxazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino](DL-5-isoxazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino][DL-3-(1,2,4-thiadiazolyl)]acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino][DL-5-(1,2,4-thiadiazolyl)]acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino][DL-5-(1-methyltetrazolyl)]acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino][DL-2-(5-chlorothienyl)]acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(aminocarbonyl)amino][DL-3-(4-methylthienyl)]acetyl]amino]-3-[[(1-methyl-1H-tetrazol-5-yl)thio]methyl]-8-oxo-5-thia-1-azabicyclo[4.2.0]oct-2-ene-2-carboxylic acid; and 7β-[[[(aminocarbonyl)amino][DL-2-(4-chloropyrryl)]acetyl]amino]-3-[[(1-methyl-1H-tetrazol-5-yl)thio]methyl]-8-oxo-5-thia-1-azabicyclo[4.2.0]oct-2-ene-2-carboxylic acid; respectively.

EXAMPLES 32-38

Following the procedure of Example 8 but substituting for the methylisocyanate one of the following:
ethylisocyanate
propylisocyanate
i-propylisocyanate
butylisocyanate
i-butylisocyanate
t-butylisocyanate
pentylisocyanate
one obtains:

7β-[[[(ethylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(propylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(i-propylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(butylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(i-butylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(t-butylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid; and 7β-[[[(pentylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid respectively.

Similarly by employing the methylisocyanate from Example 8 or the alkylisocyanates of Examples 32–38 in place of the potassium cyanate in Examples 1, 4, 6, 7, and 9 to 31 other compounds within the scope of this invention are obtained.

EXAMPLES 39-88

Following the procedures of Examples 2, 4, or 10 but employing the substituted 7-aminocephalosporanic acid derivatives shown in Col. A the products shown in Col. B are obtained.

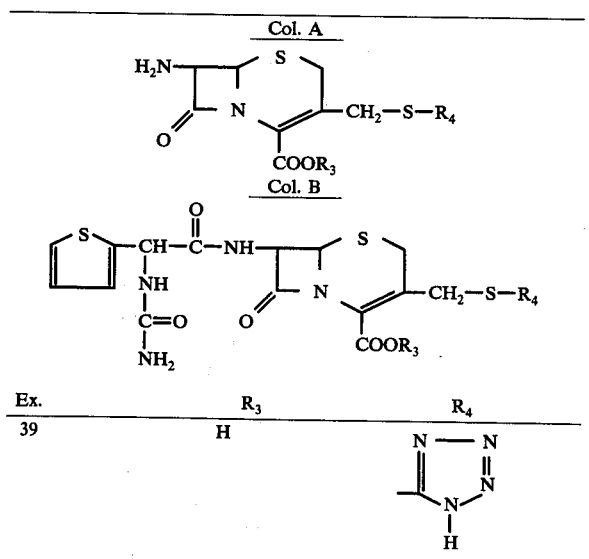

| Ex. | $R_3$ | $R_4$ |
|---|---|---|
| 39 | H | (1-methyl-1H-tetrazol-5-yl) |

-continued

Col. A: H₂N-[β-lactam-S]-CH₂-S-R₄ / COOR₃

Col. B: thiophene-CH(NHC(O)NH₂)-C(O)-NH-[β-lactam-S]-CH₂-S-R₄ / COOR₃

| Ex. | R₃ | R₄ |
|---|---|---|
| 40 | H | 1-ethyl-tetrazol-5-yl |
| 41 | H | 1-propyl-tetrazol-5-yl |
| 42 | H | 1-butyl-tetrazol-5-yl |
| 43 | -CH(C₆H₅)₂ | 1-ethyl-tetrazol-5-yl |
| 44 | t-C₄H₉ | 1-methyl-tetrazol-5-yl |
| 45 | -CH₂-C₆H₅ | 1-methyl-tetrazol-5-yl |
| 46 | -CH₂-C₆H₄-Cl (3-Cl) | 1-methyl-tetrazol-5-yl |
| 47 | -CH₂-C₆H₄-CH₃ (4-) | 1-ethyl-tetrazol-5-yl |
| 48 | -CH₂-O-C(O)-CH₃ | 1-methyl-tetrazol-5-yl |
| 49 | -CH₂-O-C(O)-CH₂-C₆H₅ | 1H-tetrazol-5-yl |
| 50 | H | 1,3,4-thiadiazol-2-yl (H) |
| 51 | H | 5-ethyl-1,3,4-thiadiazol-2-yl |
| 52 | -CH(C₆H₅)₂ | 5-propyl-1,3,4-thiadiazol-2-yl |
| 53 | -CH₂-C₆H₄-OCH₃ | 5-methyl-1,3,4-thiadiazol-2-yl |
| 54 | -CH₂-O-C(O)-C₂H₅ | 5-methyl-1,3,4-thiadiazol-2-yl |
| 55 | -CH₂-O-C(O)-C₆H₅ | 5-methyl-1,3,4-thiadiazol-2-yl |
| 56 | H | 1,3,4-oxadiazol-2-yl (H) |
| 57 | -CH(C₆H₅)₂ | 5-methyl-1,3,4-oxadiazol-2-yl |
| 58 | H | 5-methyl-1,3,4-oxadiazol-2-yl |
| 59 | H | 5-ethyl-1,3,4-oxadiazol-2-yl |
| 60 | -CH₂-O-C(O)-C₆H₄-Br | 5-methyl-1,3,4-oxadiazol-2-yl |

-continued

Col. A
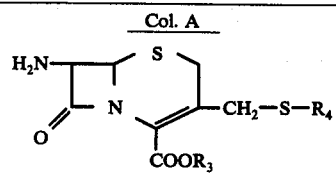
Col. B
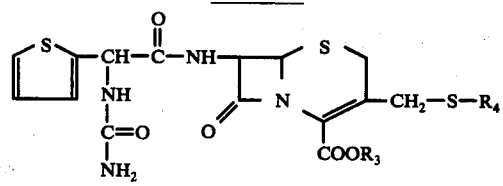

| Ex. | R₃ | R₄ |
|---|---|---|
| 61 | −CH₂−O−C(=O)−CH₂−(3-methoxyphenyl) | 2-methyl-1,3,4-oxadiazol-5-yl |
| 62 | −CH(C₆H₅)₂ | 1,3-thiazol-2-yl |
| 63 | −CH(C₆H₅)₂ | 4-methyl-1,3-thiazol-2-yl |
| 64 | H | 4-methyl-1,3-thiazol-2-yl |
| 65 | −CH₂−O−C(=O)−CH₃ | 4-ethyl-1,3-thiazol-2-yl |
| 66 | −CH(C₆H₅)₂ | 1,3,4-thiadiazol-2-yl |
| 67 | H | 1,3,4-thiadiazol-2-yl |
| 68 | t-C₄H₉ | 1,3-thiazol-2-yl |
| 69 | H | 4-methyl-1,3-thiazol-2-yl |
| 70 | H | 5-methyl-1,3-thiazol-2-yl |
| 71 | H | 5-propyl-1,3-thiazol-2-yl |

-continued

Col. A
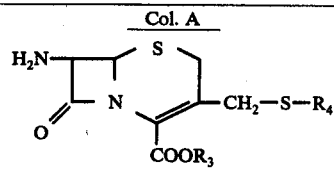
Col. B
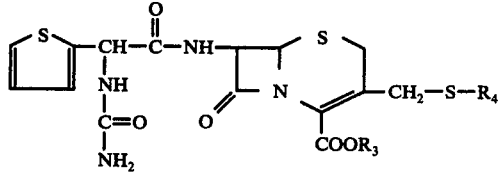

| Ex. | R₃ | R₄ |
|---|---|---|
| 72 | −CH(C₆H₅)₂ | isoxazol-3-yl |
| 73 | H | 3-methyl-isoxazol-5-yl |
| 74 | H | 4-methyl-isoxazol-3-yl |
| 75 | H | 5-ethyl-isoxazol-3-yl |
| 76 | −CH(C₆H₅)₂ | pyridyl N-oxide |
| 77 | H | pyridyl N-oxide |
| 78 | Si(CH₃)₃ | 1-methyl-tetrazol-5-yl |
| 79 | Sn(CH₃)₃ | 2-methyl-1,3,4-thiadiazol-5-yl |
| 80 | Si(C₂H₅)₃ | 2-methyl-1,3,4-thiadiazol-5-yl |
| 81 | Sn(C₂H₅)₃ | 2-methyl-1,3-triazol-5-yl (1-methyl) |

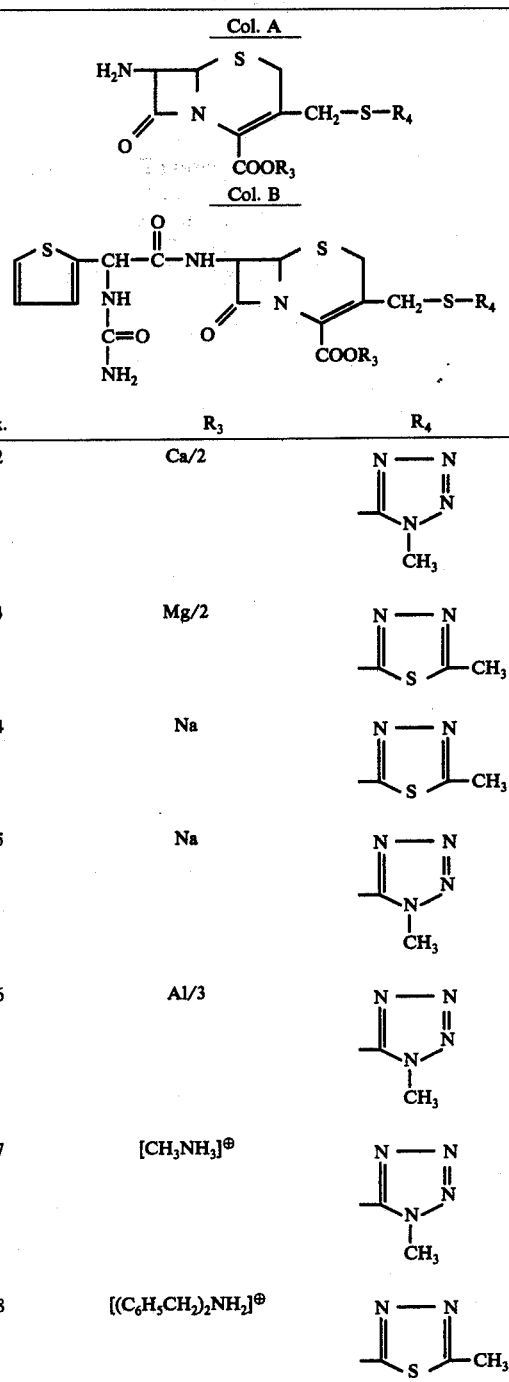

| Ex. | $R_3$ | $R_4$ |
|---|---|---|
| 82 | Ca/2 | N—N (N-methyl tetrazolyl) |
| 83 | Mg/2 | thiadiazolyl-CH₃ |
| 84 | Na | thiadiazolyl-CH₃ |
| 85 | Na | N-methyl tetrazolyl |
| 86 | Al/3 | N-methyl tetrazolyl |
| 87 | [CH₃NH₃]⊕ | N-methyl tetrazolyl |
| 88 | [(C₆H₅CH₂)₂NH₂]⊕ | thiadiazolyl-CH₃ |

These same compounds can also be prepared according to the procedures of examples 1 and 6 to 9 by substituting for the 1-methyl-1H-tetrazole-5-thiol the compound $R_4$—S—H wherein $R_4$ is as set forth above in Col. B.

What is claimed is:

1. A compound of the formula:

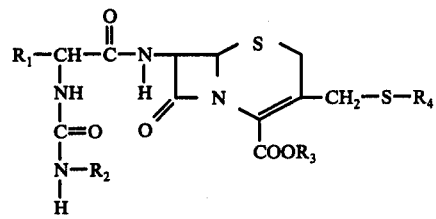

wherein $R_1$ is a hetero group attached at an available carbon atom and is selected from the group consisting of thienyl, furyl, pyrryl, pyridyl, thiazolyl, isothiazolyl, oxazolyl, isoxazolyl, thiadiazolyl, tetrazolyl and any of said heterocyclics having a Cl, Br, methyl or ethyl substituent; $R_2$ is straight or branched chain alkyl of 1 to 4 carbons; $R_3$ is selected from the group consisting of hydrogen, lower alkyl, benzyl, phenethyl, diphenylmethyl, tri(lower alkyl of 1 to 4 carbons)silyl, tri(lower alkyl of 1 to 4 carbons)stannyl, aluminum, sodium, potassium, calcium, magnesium, dibenzylamine, N,N-dibenzylethylenediamine, methylamine, triethylamine, N-ethylpiperidine, mono substituted benzyl or phenethyl wherein the substituent is Cl, Br, lower alkyl of 1 to 4 carbons, or lower alkoxy of 1 to 4 carbons, and the group

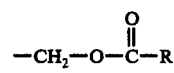

wherein R is selected from the group consisting of lower alkyl of 1 to 4 carbons, phenyl, benzyl, phenethyl, and mono substituted phenyl, benzyl, or phenethyl wherein said substituent is Cl, Br, lower alkyl of 1 to 4 carbons, or lower alkoxy of 1 to 4 carbons; and $R_4$ is selected from the group consisting of

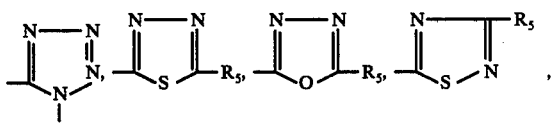

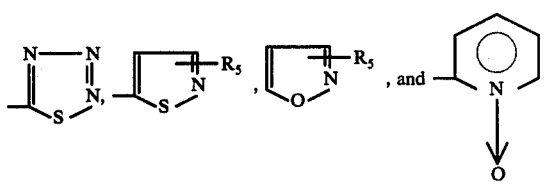

wherein $R_5$ is selected from the group consisting of hydrogen and alkyl of 1 to 4 carbons.

2. The compound of claim 1 as the D, L, or D,L-isomer wherein $R_1$ is 2-thienyl or 3-thienyl; and $R_3$ is hydrogen, sodium, or potassium.

3. The compound of claim 2 wherein $R_5$ is methyl.

4. The compound of claim 3 wherein $R_4$ is

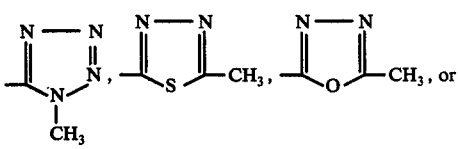

-continued

5. The compound of claim 4 wherein $R_4$ is

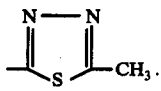

6. The compound of claim 5 wherein $R_2$ is methyl.

7. The compound of claim 4 wherein $R_4$ is

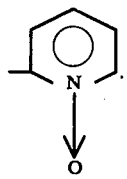

8. The compound of claim 7 wherein $R_2$ is methyl.
9. The compound of claim 8 wherein $R_1$ is 2-thienyl.
10. The compound of claim 9, 7β-[[[(methylaminocarbonyl)amino](D-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid.
11. The sodium salt of the compound of claim 8.
12. The potassium salt of the compound of claim 8.
13. The compound of claim 8 wherein $R_1$ is 3-thienyl.
14. The compound of claim 1 wherein $R_4$ is

* * * * *

UNITED STATES PATENT AND TRADEMARK OFFICE
CERTIFICATE OF CORRECTION

PATENT NO. : 4,088,816
DATED : May 9, 1978
INVENTOR(S) : Uwe D. Treuner et al.

It is certified that error appears in the above-identified patent and that said Letters Patent are hereby corrected as shown below:

Col. 3, line 67, "60-ureido compounds" should read, -- α-ureido compounds --.

Col. 5, line 8, "an cid" should read -- an acid --.

Col. 6, line 4, the names "Enterobacter" and "Proteus" should both be italicized.

Col. 6, line 5, "Serratia." should be italicized.

Col. 12, line 34, "(f) $7^b$" should read -- (f) 7β --.

Col. 12, line 44, "The $7^b$" should read -- The 7β --.

Signed and Sealed this

*Fifth* Day of *December 1978*

[SEAL]

*Attest:*

RUTH C. MASON
*Attesting Officer*

DONALD W. BANNER
*Commissioner of Patents and Trademarks*